(12) United States Patent
Paufique

(10) Patent No.: US 6,506,421 B2
(45) Date of Patent: Jan. 14, 2003

(54) PROCESS FOR THE EXTRACTION OF AN ACTIVE PRINCIPLE FROM TEGUMENTS OF APPLE, ACTIVE PRINCIPLE OBTAINED, AND COMPOSITION FOR COUNTERACTING THE CONSEQUENCES OF OXIDATIVE STRESS OF THE SKIN

(75) Inventor: Jean-Jacques Paufique, Objat (FR)

(73) Assignee: Societe Industrielle Limousine d'Application Biologique (Silab), Objat (FR)

( * ) Notice: Subject to any disclaimer, the term of this patent is extended or adjusted under 35 U.S.C. 154(b) by 0 days.

(21) Appl. No.: 09/848,265

(22) Filed: May 4, 2001

(65) Prior Publication Data

US 2002/0004080 A1 Jan. 10, 2002

(30) Foreign Application Priority Data

May 4, 2000 (FR) ............................................. 00 05726

(51) Int. Cl.$^7$ ................................................ A61K 35/78
(52) U.S. Cl. ....................................... 424/765; 424/777
(58) Field of Search .................................. 424/765, 777

(56) References Cited

U.S. PATENT DOCUMENTS 4,601,905 A * 7/1986 Szeles
5,853,728 A * 12/1998 Tanabe et al.

FOREIGN PATENT DOCUMENTS

| DE | 19619459 | * | 7/1997 |
| EP | 0 781 544 | | 7/1997 |
| JP | 09291011 | * | 11/1997 |
| RU | 2 018 316 | | 8/1994 |

OTHER PUBLICATIONS

Kootstra, A. Plant Molecular Biol. 1994. vol. 26, pp. 771–774.*
Database MEDLINE "en ligne" retrieved from STN database accession No. 97141165, XP002154645–Phytochem. vol. 43, No. 1, 1996–Abstract.

* cited by examiner

Primary Examiner—Christopher R. Tate
(74) Attorney, Agent, or Firm—Young & Thompson

(57) ABSTRACT

The present invention is a process for the extraction of an active principle for action against the consequences of oxidative stress, permitting countering cutaneous aging, characterized in that it comprises the following steps:

Figures 1, 2:
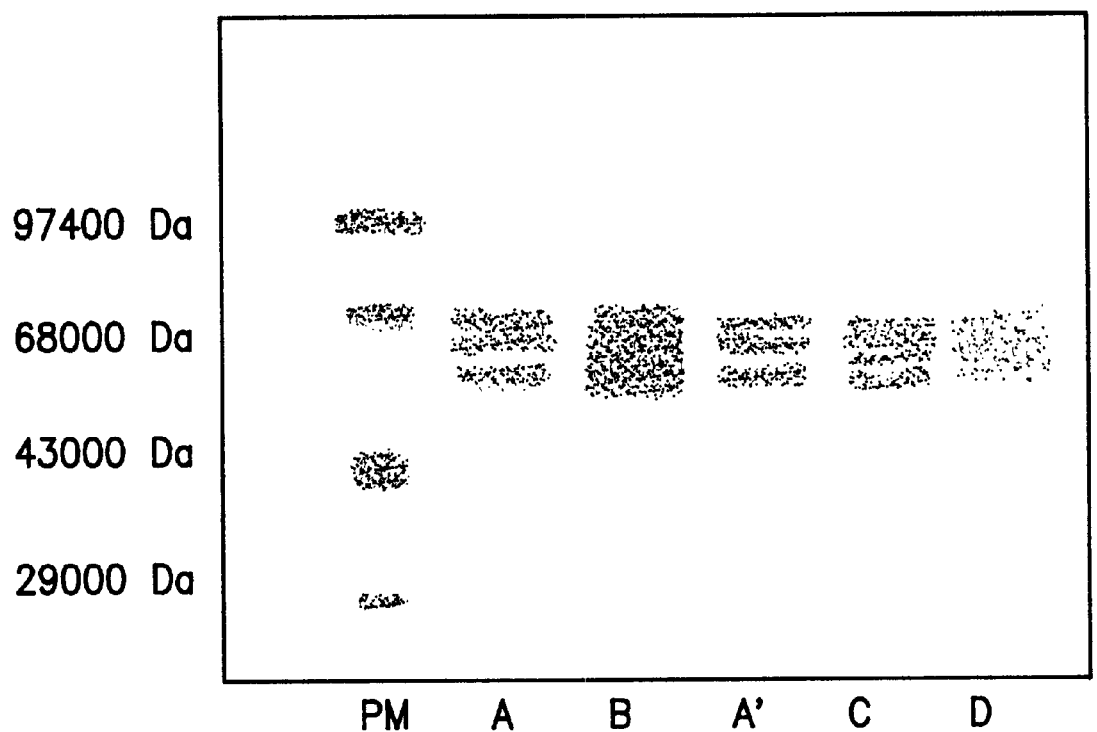

- reduction to fine powder of dried apple tegument,
- solubilization of this powder with at least 8% by volume of powder in an aqueous solution,
- conjoint enzymatic hydrolysis of the sugars and proteins,
- heating permitting total inactivation of the enzymes, and
- sterilizing filtration to retain the microorganisms, yeasts and molds as well as the total mesophilic flora.

The invention also covers the associated compositions and a process for countering accelerated aging of the skin.

20 Claims, 2 Drawing Sheets

| | % |
|---|---|
| A | 1% |
| B | 100% |
| C | −41% |
| D | −68% |

| S.t | UVA/UVB | | | | UVC | | | |
|---|---|---|---|---|---|---|---|---|
| | X | Y | FM | RFM | X | Y | FM | RFM |
| TNI | 312 | 549 | 0.57 | – | 312 | 548 | 0.57 | – |
| TI | 946 | 359 | 2.63 | 100 | 1965 | 298 | 6.58 | 100 |
| P.A. 1% | 1053 | 323 | 3.27 | 124 | 1765 | 373 | 4.73 | 72 |
| P.A. 2% | 696 | 429 | 1.62 | 62 | 1657 | 401 | 4.13 | 63 |

FIG. 3A

| E.c | UVA/UVB | | | | UVC | | | |
|---|---|---|---|---|---|---|---|---|
| | X | Y | FM | RFM | X | Y | FM | RFM |
| TNI | 47 | 377 | 0.13 | – | 312 | 548 | 0.57 | – |
| TI | 75 | 337 | 0.22 | 100 | 193 | 313 | 0.62 | 100 |
| P.A. 1% | 65 | 219 | 0.30 | 136 | 149 | 197 | 0.76 | 122 |
| P.A. 2% | 59 | 450 | 0.13 | 59 | 141 | 383 | 0.13 | 60 |

FIG. 3B

PROCESS FOR THE EXTRACTION OF AN ACTIVE PRINCIPLE FROM TEGUMENTS OF APPLE, ACTIVE PRINCIPLE OBTAINED, AND COMPOSITION FOR COUNTERACTING THE CONSEQUENCES OF OXIDATIVE STRESS OF THE SKIN

The present invention relates to a process for the extraction of an active principle from teguments of apple and the active principle obtained. This active principle, in a suitable composition also claimed, particularly for cosmetological applications, permits counteracting the effects of oxidative stress of the skin, which is to say against cutaneous aging of the skin.

It is known that free radicals of oxygen give rise to pathologies, more particularly at the cutaneous level, still more particularly during aging. Such free radicals can arise from different endogenous actions (activation of the arachidonic acid metabolism, phagocytosic activation or accumulation of reduced metabolites), or exogenous (radiation, UV radiation, air pollution or certain smoke, particularly of cigarettes).

As a function of the magnitude of the oxidative stress, there can be a suitable defense by liberation of anti-oxidant enzymes in a quantity sufficient to compensate the actions of the generated free radicals.

These free radicals are neutralized in the cells thanks to chemical or enzymatic means, particularly anti-oxidant systems which permit them to protect themselves and to be regulated against harmful effects of these radicals.

Nevertheless, beyond a certain threshold, the anti-oxidant systems are no longer sufficient and are submerged by the radical flow leading to irreversible cellular damage. It is also known that age plays a large role and that the anti-oxidant systems are less and less effective to guard against free radicals produced in large quantity.

The damage to the cell occasioned by uncontrolled oxidative stress is essentially of three types:

1/ OXIDATION OF THE CELLULAR PROTEINS

This oxidation is associated with a parallel inactivation of the enzymatic system, leading to proteic fragmentation. The proteic modifications are generally initiated by OH radicals and the oxidation processes take place by intervention of the $O_2$ and $O_2^-$ radicals.

Such an oxidation takes place according to three mechanisms:

- oxidation by the free radicals of the side chains of amino acids. More particularly the aromatic amino acids are oxidized into carbonyl derivatives. Furthermore, the reactions such as glycation or peroxidation take part in the oxidation of the proteins.
- rupture of the peptide links which leads to fragmentation of the proteins and to the formation of inactive peptide segments.
- formation of covalent cross bonds between proteins, under the influence of free OH radicals, promoted by disulfide or tyrosine bridges. These damaged proteins thus modified in their structure as in their function, are inactivated.

2/ DNA LESIONS OF THE CELL NUCLEI

Helical DNA chains are permanently endangered as to their integrity by endogenous free radicals, chemical agents, and different UV radiations.

Such lesions prevent the good functioning of the cells and can lead to genetic mutations.

There exists a system of repair of damaged DNA, particularly by excision, but the risks of genetic mutation remain if the lesion is not recognized or if its repair is not complete.

It is also necessary to protect the DNA molecules and to limit the UV induced mutations.

3/ MEMBRANE PEROXIDATION OF THE CELL

The membrane of the cell is less protected and remains the privileged target of free radicals, which lead to peroxidation of the polyunsaturated fatty acids of the phospholipidic membranes. There is thus the formation of cytotoxic peroxides which lead to membrane permeability and the death of the cell.

These three actions lead to major damages that are intense, targeted and above all irreversible.

Also, numerous natural or synthetic anti-oxidants are used to attempt to mitigate the actions of the free radicals.

On the other hand, these anti-oxidants each have one or more specific activities but against a well-defined group of free radicals or acting through targeted mechanisms on certain oxidated sequences such that it is difficult to act simultaneously on all of the effects of oxidative stress.

Thus, an anti-oxidant which inhibits lipidic peroxidation has no action on oxidation of the proteins or DNA lesions.

This is one of the principal interests of the active principle according to the present invention, which permits acting simultaneously against these three factors and hence permits acting against cutaneous aging.

The present invention covers a process for the extraction of this active principle.

To this end, the extraction process of an active principle according to the invention, for taking action against the consequences of oxidative stress permitting counteracting cutaneous aging, is characterized in that it comprises the following steps:

- reduction to fine powder of dried apple tegument,
- solubilization of this powder with a minimum of 8% volume of powder, in an aqueous solution,
- conjoint enzymatic hydrolysis of the sugars and proteins,
- heating, permitting total inactivation of the enzymes, and
- sterilizing filtration to retain the microorganisms, yeasts, and molds as well as the total mesophilic flora.

The obtained solution can be concentrated lyophilized or atomized.

The invention also covers the active principle obtained by this process and at least one cosmetic composition to guard simultaneously against cellular protein oxidation, against mutations induced by UV radiation and against membrane peroxidation of the cells of the skin, this composition comprising this active principle associated in an suitable galenic form.

The invention also covers a process to combat cutaneous aging, which consists in applying preventatively to the skin such a cosmetic composition.

The different accompanying drawing figures show results obtained during different tests of the characterization of the extracted active principle and of its activity.

FIG. 1 shows a condition on a plate of the results of chemiluminescence of the oxidations of different proteins, FIG. 2 shows a table of the decrease of oxidation quantities, and FIGS. 3A and 3B show effects against mutations induced by UV radiation in the case of *Salmonella typhimurium* and of *Escherichia coli*.

The extraction process according to the invention will now be described in detail, followed by the characteristic of the active principle and of the tests.

1/ EXTRACTION PROCESS

The extraction process of the active principle according to the present invention consists in the sequence of the following steps:

reduction to a fine powder of dried apple tegument,
solubilization of this powder at a minimum of 8% by volume of powder in an aqueous solution,
conjoint enzymatic hydrolysis of the sugars and proteins,
heating, more particularly for a duration of 20 minutes to 6 hours, at a temperature comprised between 50 and 80° C., permitting total inactivation of the enzymes,
if desired concentration of the obtained solution,
sterilize in filtration to retain the microorganisms, yeasts, and molds, as well as the total mesophilic flora.

The solution can be concentrated without this being a necessity or even can be lyophilized or atomized.

II/ CHARACTERIZATION OF THE ACTIVE PRINCIPLE

The active principle from this process is characterized by the following composition and by the following characteristics:

1/ Dried material:

The quantity of dried material is greater than 100 g/l, particularly comprised between 100 and 300 g/l and more particularly between 140 and 200 g/l. This range is determined by passage through the stove at 105° C. until a constant weight is obtained.

2/ pH:

The value of the pH is comprised between 4.0 and 10.0, more particularly between 5.0 and 7.0, obtained by the potentiometric method at constant temperature.

3/ Total sugar content:

The total sugar content is obtained by the DUBOIS method (DUBOIS M et al. (1956) Analytical Chemistry, 28, No. 3, pp. 350–356).

In the presence of phenol and concentrated sulfuric acid, the reducing sugars give an orange-yellow compound.

After cooling, the optical density is read on the spectrophotometer at 490 nm.

A test curve is established with a range from a combination of 1/3 of manose, 1/3 of glucose and 1/3 of galactose, with concentrations of 25 to 100 µg/l.

The values of the quantities of sugar are read on the curve directly and in the case of the active principle according to the present invention, there are obtained total sugar values comprised between 40 and 300 g/l, preferably between 80 and 160 g/l.

4/ Total polyphenols:

The phenolic compounds form colored complexes in the presence of potassium ferricyanide, whose intensity can be detected at 715 nm. This permits determining the quantity of phenolic compounds on a curved scale. This curve is obtained from a scale range for gallic acid, from 40 to 120 mg/l.

The content of phenolic compounds is thus expressed in mg of gallic acid.

The value obtained is comprised between 900 and 2000 mg/l.

5/ Stability

The obtained active principle is stable at a pH greater than 4.0.

The active principle is stable at a temperature up to 80° C.

The active principle is also stable in an ethanol/water mixture up to the concentration of 40% by volume of ethanol, which is to say for concentrations of 3.5 or 7% of active principle.

III/ EFFECTS OF THE EXTRACTED ACTIVE PRINCIPLE AND CHARACTERIZED TO COMBAT CUTANEOUS AGING

It is shown by experiments and the following tests that the active principle according to the invention has activities permitting it to counter the three factors set forth above in the preamble.

1/ Effect against cellular protein oxidation

The study consists in evaluating the protective activity of the active principle. It is conducted by measuring the quantity of oxidation of the explanted proteins subjected to UVA+UVB irradiation.

The explants are placed in contact with the products 2 hours before irradiation and during irradiation. A concentration of active principle is from 5 to 7%.

Analyses are carried out 24 hours after irradiation.

The protocol consists in substituting dinitrophenol on the carbonyl groups which are characteristic of the oxidized proteins.

Then the dinitrophenol is removed with an anti-dinitrophenol antibody.

Derivatization of the carbonyl groups is carried out with an Oxyblot coupling solution, sold by the American company Oncor, for 30 minutes at 20° C.

After neutralization, the specimens are transferred onto Immobilon, sold by the French company Polylabo.

Once the membrane is saturated and incubated with the anti-dinitrophenol antibodies, then conjugated with an anti-immunoglobulin of rabbit-peroxidase, both from the Oncor company, it is revealed by chemiluminescence and the density of the bands of the recovered images is quantified.

The proteins of each extract are also determined.

The study shows that there exist naturally oxidized proteins, because the non-irradiated specimens also have proteic bands between 50,000 and 70,000 Daltons, which corresponds to the oxidized proteins. Refer to FIG. 1, which shows the results of the film after chemiluminescence.

PM: Molecular weight,

A: Non-irradiated specimen,

B: Irradiated specimens,

A': Non-irradiated specimen in contact with the active principle at 7%,

C: Irradiated specimen in contact with the active principle at 5%, and

D: Irradiated specimen in contact with the active principle at 7%.

The irradiated explant specimen has much greater oxidation of the proteins.

Moreover, it will be noted that the oxidation is less in the case of explants that are irradiated but in contact with the active principle according to the present invention. Moreover, this decrease is proportional to the concentration of the active principle.

The results are found in the table of FIG. 2.

2/ Effect against mutations induced by UV radiation

The study has for its object to show the antimutagenic activity of the active principle according to the present invention as to mutations induced by UV radiation.

The protocol consists in subjecting a bacterial suspension of *Salmonella typhimurium* (TA 102) and of *Escherichia coli* (WP2) to UVA/UVB or UVC radiation.

Then a portion of these irradiated suspensions is poured into a Petri dish with two types of medium:

a/ minimum agar medium to estimate the reverting colonies, X b/ nutrient agar medium to estimate the viable colonies, Y.

After incubation, the colonies are counted by means of a suitable apparatus.

The frequency of mutation is then computed, which is the ratio of the number of reverting colonies to the number of viable colonies X/Y and the frequency of relative mutation (FRM) which is the ratio of the frequency of mutation ($FM_{sup}=X_{sup}/Y_{sup}$) of the irradiated suspension but treated with the active principle according to the present invention, to the frequency of mutation of the irradiated specimen that is however not treated ($FM_{spec}=X_{spec}/Y_{spec}$)

The results are shown in the tables of FIGS. 3A and 3B respectively, for *Salmonella typhimurium* and *Escherichia coli*.

The active principle has an anti-mutagenic potential as to mutations induced by UVA, UVB and UVC.

3/ Effect of DNA protection:

The study seeks to determine the genoprotective effect of the active principle according to the present invention.

To this end, there is carried out an in vitro test so-called test 3D (Damaged DNA Detection) and sold by the French company "SFRI Laboratory" to detect genotoxic agents by repairing the DNA lesions by reproducing in vitro the repair process for said lesions.

In this test, HELA cells are cultured then incubated with 2 or 4% of the active principle. An attack is carried out by means of a solution of oxygenated water.

The cells are then lysated and then genomic DNA is recovered and analyzed.

The test 3D consists in a repair of the lesions by protein complexes that are specific to repair. A nucleotide marked with biotin is incorporated in the DNA during resynthesis.

A recognition of the biotin by means of an avidin molecule coupled to a peroxidase, then development by addition of a chemiluminescent substrate of peroxidase.

A luminometer then permits detecting and measuring the intensity of this luminescence.

The results show a percentage of inhibition of the lesion effect of 22% and 75% respectively, for doses of active principle of 2% and 4% on the HELA cells.

The active principle according to the invention thus has a great anti-lesion activity.

4/ Effect on the appearance of sunburn cells:

"Sunburn cells" are dyskeratosic keratinocytes of the epidermis which appear after UV irradiation.

These cells have DNA lesions and are in apoptosis.

The operational protocol provides on the one hand setting aside non-irradiated specimens and on the other hand irradiating with UVA and UVB explants subjected to the presence of 5% and 7% of active principle according to the present invention.

After rinsing and fixation, histological cutting and coloration, the "sunburn cells", which is to say the apoptotic keratinocytes, are counted with a microscope.

There is seen a percentage of reduction of 49% and 63% of the ratio of the number of "sunburn cells" relative to the irradiated specimen.

The skin is thus protected from the deleterious effects of free radicals induced by UV.

5/ Protective effect of the fibroblasts and of keratinocytes subjected to UV

Keratinocytes and fibroblasts are cultivated in suitable media.

These cells are irradiated with UVA and UVB.

The cellular viability permits estimating the protective effect of the active principle according to the present invention.

Fibroblasts: Anti-radicular activity is 30, 68 and 86%, respectively, during contacting with 1, 3 and 5% of active principle.

Keratinocytes: Anti-radicular activity is 53, 90 and 100% respectively, during contacting with 1, 3 and 5% of active principle.

The active principle according to the present invention permits acting against the three factors simultaneously and at quite high levels.

The active principle can be integrated into cosmetic compositions in the amount of 0.1% to 10% by weight.

A process for acting against cutaneous aging consists in placing on the skin a cosmetic composition including between 0.1% and 10% by weight of active principle according to the present invention.

What is claimed is:

1. A process for extracting an active principle which inhibits cutaneous agina attributable to oxidative stress, comprising:

reducing dried apple tegument to a fine powder, solubilizing said powder with a minimum of 8% by volume of powder in an aqueous solution to form a mixture, subjecting said mixture to enzymatic hydrolysis, heating said mixture to inactivate the enzymes, and sterile filtering said mixture to obtain a solution free of microorganisms, yeasts, molds and mesophilic flora.

2. The process according to claim 1, wherein the heating step consists of heating said mixture for a period of 20 minutes to 6 hours at a temperature between 50 and 80° C.

3. The process according to claim 1, further comprising concentrating, lyophilizing or atomizing said solution.

4. An active principle obtained by the process of claim 1, comprising:

a quantity of dry materials greater than 100 g/l, a pH between 4.0 and 10.0, a total sugar content between 40 and 300 g/l, and a total quantity of polyphenols between 900 and 2000 g/l.

5. A cosmetic composition which acts simultaneously against cellular protein oxidation, comprising said active principle according to claim 4.

6. A cosmetic composition which counteracts mutations induced by UV radiation, comprising the active principle according to claim 4, concentrated or dried.

7. A cosmetic composition which counteracts membrane peroxidation of skin cells, comprising the active principle according to claim 4, concentrated or dried.

8. A process for counteracting cutaneous aging, comprising administering to a person a cosmetic composition according to claim 5, having 0.1 to 10% by weight of said active principle.

9. An active principle obtained by the process of claim 1, comprising:

a quantity of dry materials greater than 100 g/l, a pH between 4.0 and 10.0, a total sugar content between 40 and 300 g/l, and a total quantity of gallic acid between 900 and 2000 g/l.

10. A cosmetic composition which acts simultaneously against cellular protein oxidation, comprising said active principle according to claim 9.

11. An active principle obtained by the process of claim 1, comprising:

a quantity of dry materials between 100 g/l and 300 g/l, a pH between 5.0 and 7.0, a total sugar content between 80 and 160 g/l, and a total quantity of polyphenols between 900 and 2000 g/l.

12. A process for extracting an active principle which inhibits cutaneous aging attributable to oxidative stress comprising:

reducing dried apple tegument to a fine powder, solubilizing said powder in an aqueous solution to form a mixture, subjecting said mixture to enzymatic hydrolysis, heating said mixture to inactivate the enzymes, and sterile filtering said mixture to obtain a solution.

13. The process according to claim 12, wherein the heating step consists of heating said mixture for a period of 20 minutes to 6 hours at a temperature between 50 and 80° C.

14. An active principle obtained by the process of claim 12, comprising:

a quantity of dry materials greater than 100 g/l, a pH between 4.0 and 10.0, a total sugar content between 40 and 300 g/l, and a total quantity of polyphenols between 900 and 2000 g/l.

15. A cosmetic composition which acts simultaneously against cellular protein oxidation, comprising said active principle according to claim 14.

16. A process for counteracting cutaneous aging, comprising administering to a person a cosmetic composition according to claim 15, having 0.1 to 10% by weight of said active principle.

17. An active principle obtained by the process of claim 12, comprising:

a quantity of dry materials between 100 g/l and 300 g/l, a pH between 5.0 and 7.0, a total sugar content between 80 and 160 g/l, and a total quantity of polyphenols between 900 and 2000 g/l.

18. A cosmetic composition which acts simultaneously against cellular protein oxidation, comprising said active principle according to claim 17.

19. An active principle obtained by the process of claim 12, comprising:

a quantity of dry materials between 100 g/l and 300 g/l, a pH between 5.0 and 7.0, a total sugar content between 80 and 160 g/l, and a total quantity of gallic acid between 900 and 2000 g/l.

20. A cosmetic composition which acts simultaneously against cellular protein oxidation, comprising said active principle according to claim 18.

* * * * *